United States Patent [19]
Stavinski et al.

[11] Patent Number: 5,948,406
[45] Date of Patent: Sep. 7, 1999

[54] IMMUNOGENS, ANTIBODIES FORMED THEREFROM, AND COATING ANTIGENS USEFUL IN A DIACYLHYDRAZINE IMMUNOASSAY METHOD

[75] Inventors: Stanley Stephen Stavinski, Telford; Shuguang Wu, North Wales, both of Pa.; James Douglas Thacker, Manassas; Ellen Schalk Casale, Ashburn, both of Va.

[73] Assignee: Rohm and Haas Company, Philadelphia, Pa.

[21] Appl. No.: 08/907,318

[22] Filed: Aug. 6, 1997

Related U.S. Application Data

[60] Provisional application No. 60/023,900, Aug. 12, 1996.

[51] Int. Cl.$^6$ .................. A61K 39/395; A61K 39/00; C07K 16/00; C07C 24/00
[52] U.S. Cl. ................... 424/130.1; 424/184.1; 424/193.1; 530/387.1; 530/391.1; 530/391.5; 564/310; 564/311
[58] Field of Search .................. 424/130.1, 184.1, 424/193.1; 530/387.1, 388.9, 391.1, 391.5; 564/310, 311

[56] References Cited

U.S. PATENT DOCUMENTS

| | | | |
|---|---|---|---|
| 5,354,762 | 10/1994 | Hsu et al. | 514/338 |
| 5,358,966 | 10/1994 | James, Jr. et al. | 514/615 |
| 5,424,333 | 6/1995 | Wing | 514/615 |
| 5,530,028 | 6/1996 | Lidert et al. | 514/649 |

FOREIGN PATENT DOCUMENTS

| | | |
|---|---|---|
| 0824014 | 2/1998 | European Pat. Off. . |

OTHER PUBLICATIONS

Williams et al. Jour. Biol. Chem., 1997, vol. 272, pp. 8427–8432.

Nelson, J., Karu, A., Wong, R., *Immunoanalysis of Agrochemicals*, ACS Symposium Series, 586, pp. 288–300 (Mar. 13–17, 1994).

Hammock, B., Mumma, R., *Potential of Immunochemical Technology for Pesticide Analysis*, ACS Symposium Series, 136, pp. 321–352 (1980).

Brady, J.F., Fleeker, J.R., Wilson, R.A. and Mumma, R.O., *Enzyme Immunoassay for Aldicarb*, ACS Symposium Series, 382, pp. 262–284 ((1989).

Clausen, J., "Immunochemical Techniques for the Identification and Estimation of Macromolecules," *Laboratory Techniques in Biochemistry and Molecular Biology*, vol. 1, Part 3, R.H. Burton and P.H. Knippenberg (editors) (1991).

Currie, L.A., "Limits for Qualitative Detection and Quantitative Determination," *Analytical Chemistry*, vol. 40, No. 1, pp. 586–593 (Jan. 1968).

Fahey, J.L., Horbett, A.P., "Human Gamma Globulin Fractionation on Anion Exchange Cellulose Columns," *The Journal of Biological Chemistry*, vol. 234, No. 10, pp. 2645–2651 (Oct. 1959).

Ishikawa, E., *Journal of Immunoassay*, 4(3), pp. 209–327 (1983).

(List continued on next page.)

*Primary Examiner*—Ponnathapura Achutamurthy
*Attorney, Agent, or Firm*—John Lemanowicz; Thomas Rogerson

[57] ABSTRACT

The present invention provides an immunogen, antibodies, kits and methods of using the same to measure diacyl hydrazine compounds. The methods are easy to use, inexpensive and provide suitable cross-activity and sensitivity to enable use under FIFRA guidelines.

20 Claims, 10 Drawing Sheets

OTHER PUBLICATIONS

Salmon, S.E., Mackey, G., Fudenberg, H.H., "'Sandwich' Solid Phase Radioimmunoaasay for the Quantitative Determination of Human Immunoglobins," *The Journal of Immunology*, vol. 103, No. 1, pp. 129–137 (Jul. 1969).

Schlaeppi, J.M., Moser, H., Ramsteiner, K., "Determination of Metolachlor by Competitive Enzyme Immunoassay Using a Specific Monoclonal Antibody," *Journal of Agric. Food Chem.*, vol. 39, No. 8, pp. 553–536 (1991).

U.S. EPA, "Definition and Procedure for the Determination of the Method Detection Limit Revision 1.11." In *Federal Register*, vol. 49, No. 209, Part 136, Appendix B, Friday, Oct. 26, 1984.

U.S. EPA Pesticide Assessment Guidelines, Subdivision N. Chemistry, Enviraonmental Fate. EPA 540/9–82–021, Oct. 18, 1982.

U.S. EPA, Pesticide Assessment Guidelines, Subdivision O. Residue Chemistry. EPA 540/.9–82–023, Oct., 1982.

Voller, A., Bidwell, D.E., Bartlett, A., "Enzyme immunoassays in Diagnostic Medicine," *Bulletin, World Health Organization*, vol. 53, pp. 55–65 (1976).

IMMUNOGENS, ANTIBODIES FORMED THEREFROM, AND COATING ANTIGENS USEFUL IN A DIACYLHYDRAZINE IMMUNOASSAY METHOD

This application claims the benefit of U.S. provisional application Ser. No. 60/023,900 filed Aug. 12, 1996.

The present invention relates to an immunoassay method for measuring diacyl hydrazine compounds.

Methods for the measurement of diacyl hydrazine compounds are known. For instance, high pressure liquid chromatography (HPLC), gas liquid chromatography(GLC), GC-Mass Spectrometry, and HPLC-Mass Spectrometry are but a few of the currently available methods. However, these methods suffer several disadvantages. These methods generally require expensive and complicated instrumentation. Furthermore, sample preparation and actual analysis can be quite lengthy and require chemists and technicians specifically trained for such methods. Moreover, such prior art methods do not enable rapid screening for analogs or metabolites or both in the same step. Rather, a separation of individual compounds is generally required before detection occurs. Consequently, these methods are impracticable for rapid low cost measurements such as required, for instance in field testing or for large volume testing.

Diacyl hydrazine compounds find particular use as pesticides. Specifically, as caterpillar molt accelerating compounds (MAC). As with all potentially hazardous chemicals, such pesticides are regulated by governmental entities. During the process of obtaining regulatory approval residue analysis may be required under the Federal Insecticide, Fungicide and Rodenticide Act (FIFRA) Registration Guidelines, Subdivision O which necessitates an assay which has suitable sensitivity for such use. Furthermore, the assay must have adequate cross reactivity to the major metabolic products of the diacyl hydrazine pesticides so as to be suitable for use in metabolic and environmental fate studies as may be required in FIFRA Registration Guidelines, Subdivision N. Assays may also be required for monitoring usage of the pesticides.

Consequently, there is a need for a diacyl hydrazine assay which has sufficient sensitivity and cross reactivity to meet FIFRA Guidelines, enables rapid screening and is simple and inexpensive to use.

The present inventors have developed an immunochemical assay which is sufficiently sensitive and has sufficient cross-reactivity to qualify for usage under the FIFRA Guidelines. Moreover, the assay is simple and inexpensive to use.

In a first aspect of the invention, there is provided an immunogen, comprising:
a compound of the formula

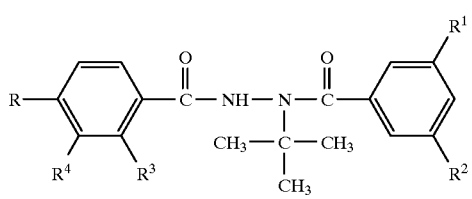

wherein R, $R^1$, $R^2$, $R^3$, and $R^4$ are each independently, hydrogen, ($C_1$–$C_6$) alkyl and substituted ($C_1$–$C_6$) alkyl, ($C_2$–$C_6$) alkenyl and substituted ($C_2$–$C_6$) alkenyl, ($C_1$–$C_6$) alkoxy, ($C_1$–$C_6$) alkyloxy, and halide; conjugated to a carrier material.

In a second aspect of the invention, there is provided a method of measuring diacyl hydrazines or derivatives thereof, comprising the steps of (A) providing a sample comprising an unknown amount of diacyl hydrazines; (B) contacting the sample with antibodies having binding affinity to diacyl hydrazine antigens in the presence of immobilized diacyl hydrazine antigen so as to form bound and unbound antibody-antigen complexes; (C) separating the unbound antibody-antigen complexes from the bound antibody-antigen complexes; (D) labeling the bound antibody complex with a detectable label; (E) effecting a measurable change in the label; and (F) measuring the diacyl hydrazines in the sample.

In a third aspect of the invention, there is provided a method of measuring diacyl hydrazines or derivatives thereof, comprising the steps of (A) providing a sample comprising an unknown amount of diacyl hydrazines; (B) contacting the sample with immobilized antibodies having binding affinity to diacyl hydrazine antigen to form immobilized antibody-antigen complexes; (C) contacting diacyl hydrazine antigen labeled with a detectable label with uncomplexed immobilized antibodies to form labeled antibody-antigen complexes; (D) effecting a measurable change in the label; and (E) measuring the diacyl hydrazines in the sample.

In a fourth aspect of the present invention, there is provided a kit for measuring diacyl hydrazines comprising (A) antibodies having binding affinity to diacyl hydrazines; (B) a label capable of binding to the antibodies; and (C) a substrate capable of producing a measurable change in the presence of the label.

BRIEF DESCRIPTION OF THE DRAWINGS

FIG. (1) depicts a protein elution profile from the DEAE ion exchange column.

FIG. (2) depicts an inhibition curve for RH2703.

Figure 1:
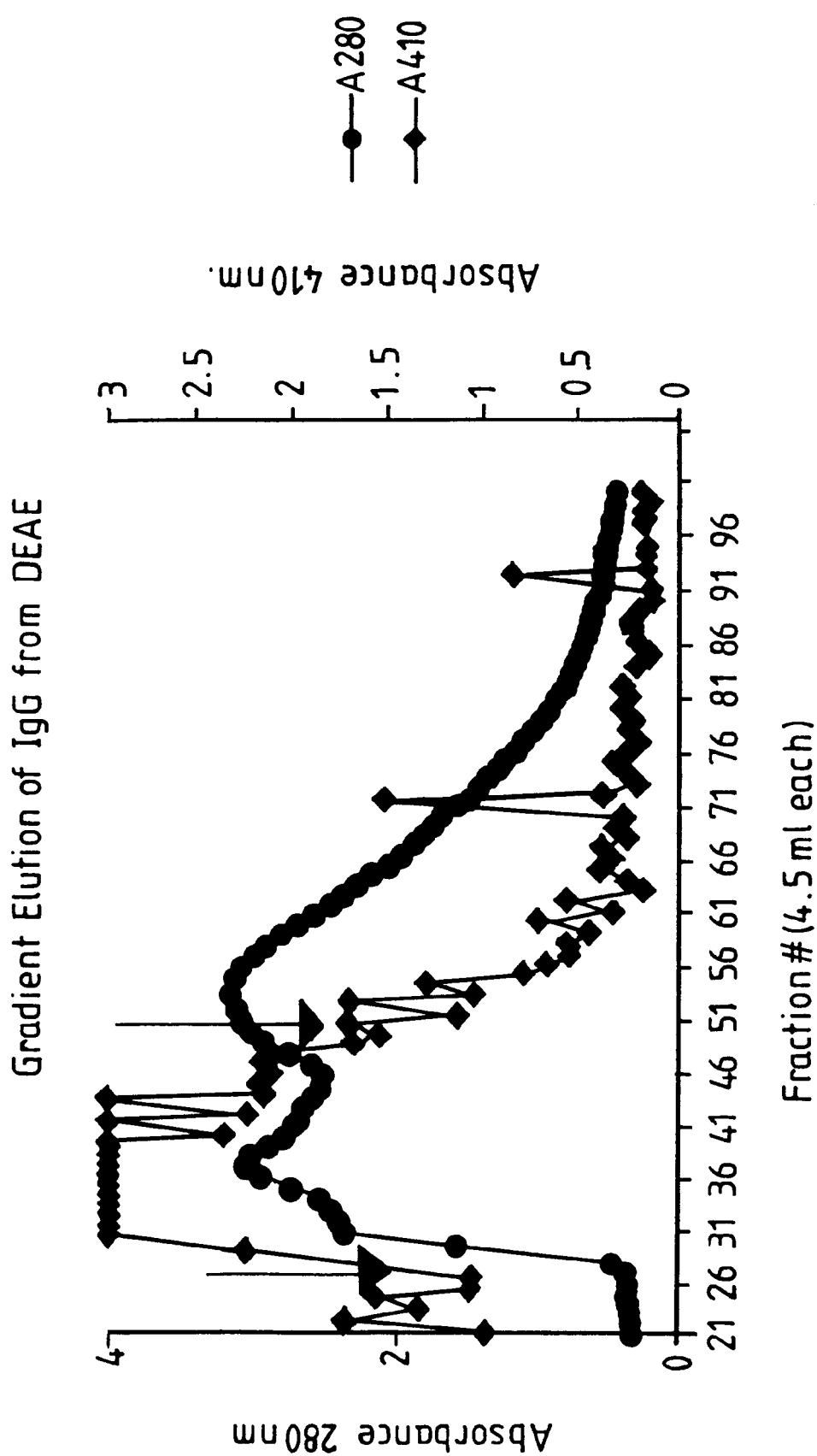
Figure 2:
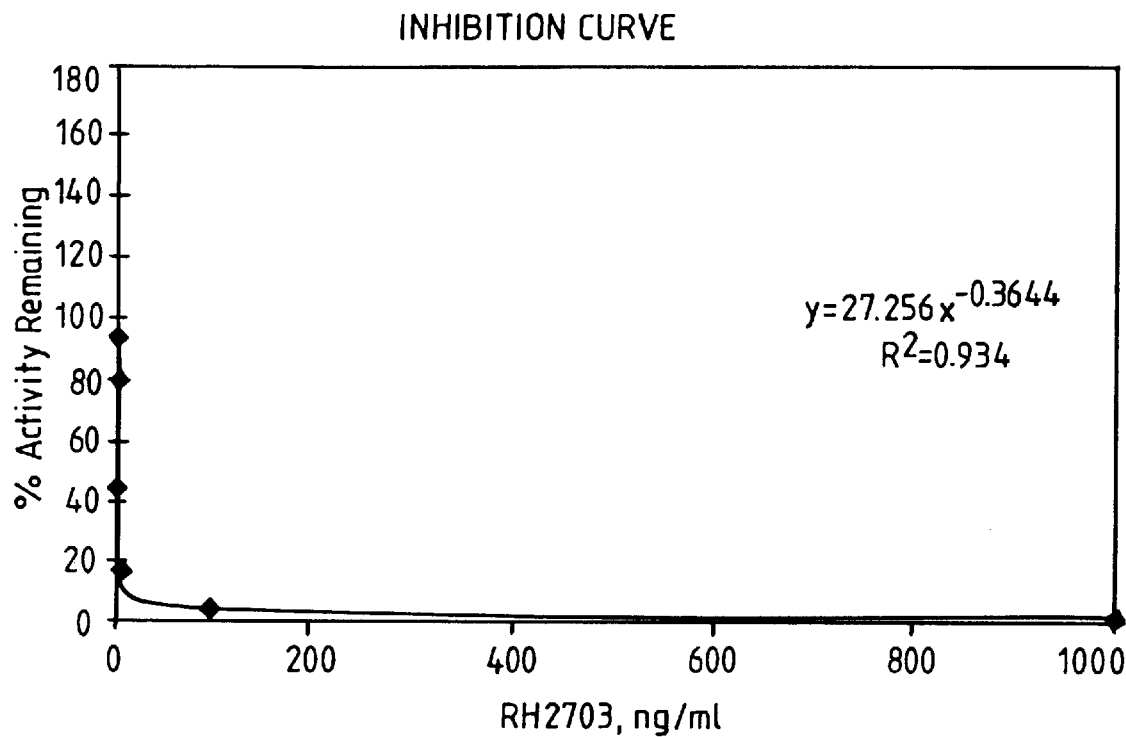
Figure 3:
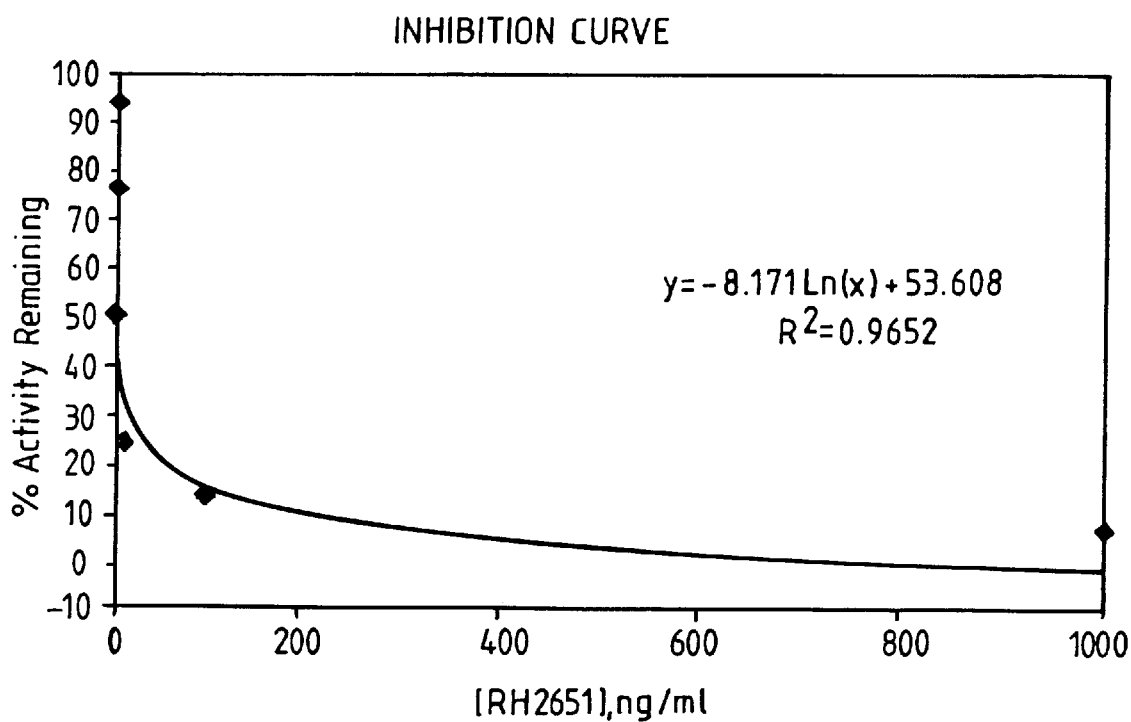
Figure 4:
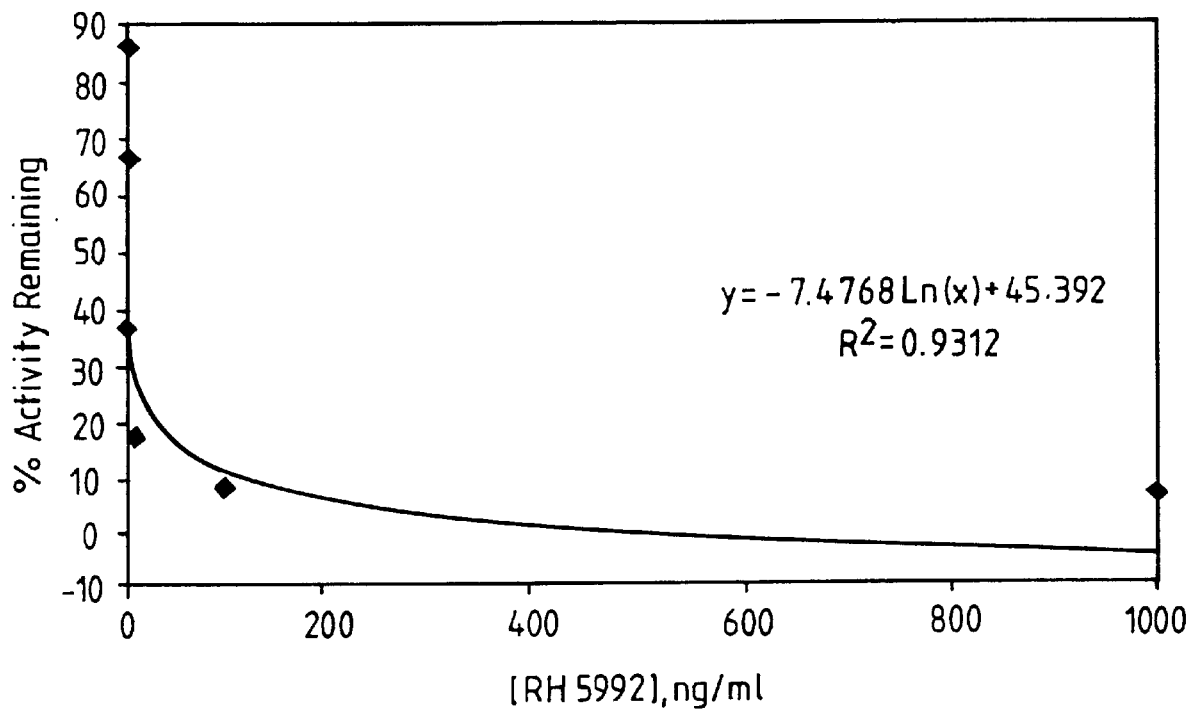
Figure 5:
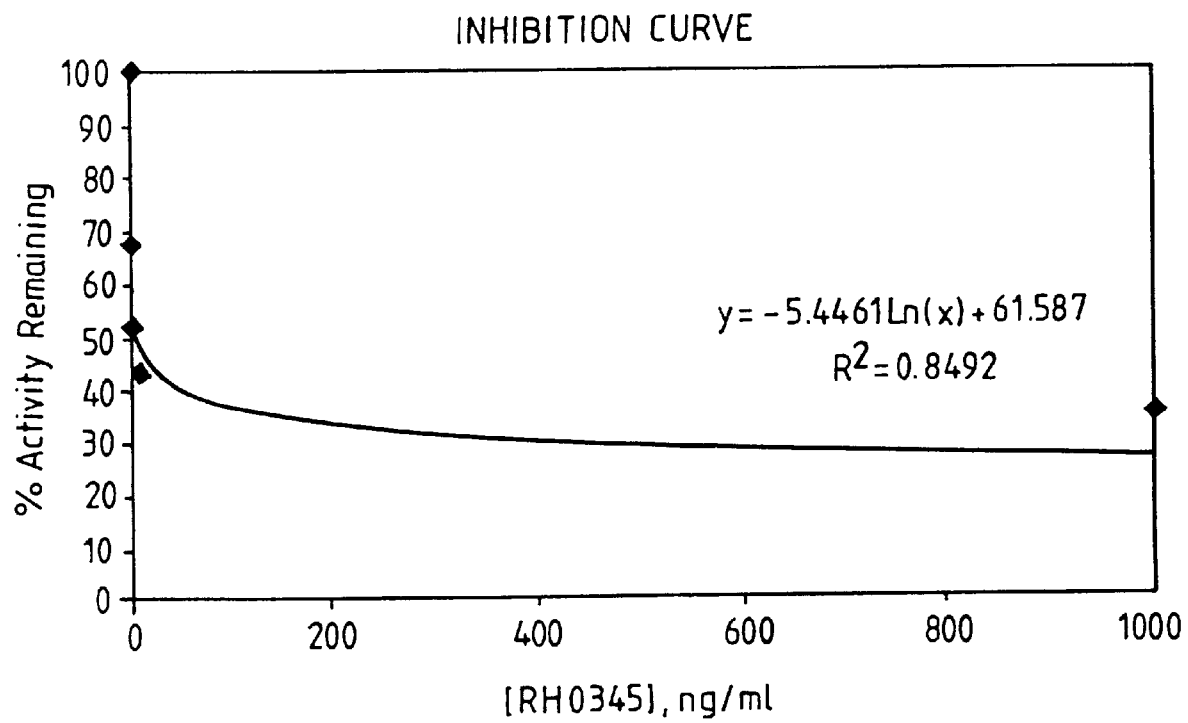
Figure 6:
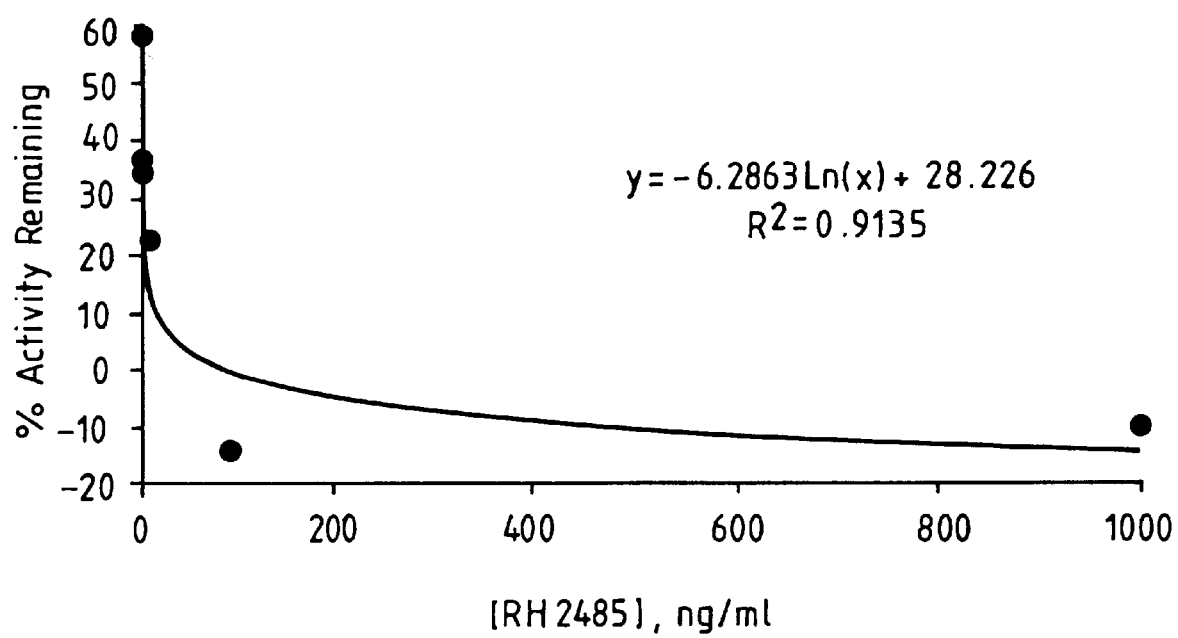

FIG. (3) depicts an inhibition curve for RH2651.

FIG. (4) depicts an inhibition curve for RH5992.

FIG. (5) depicts an inhibition curve for RH0345.

FIG. (6) depicts an inhibition curve for RH2485.

FIG. (7) depicts external standard curves obtained in PBST and matrix blank samples.

FIG. (8) depicts a calculated linear regression line for Broccoli sample 20139-01.

FIG. (9) depicts a calculated linear regression line for Broccoli sample 20139-02.

FIG. (10) depicts a calculated linear regression line for Broccoli sample 20139-04.

FIG. (11) depicts a calculated linear regression line for Broccoli sample 20139-05.

FIG. (12) depicts a calculated linear regression line for soil sample 151.

FIG. (13) depicts a calculated linear regression line for soil sample 157.

FIG. (14) depicts a calculated linear regression line for soil sample 175.

FIG. (15) depicts a calculated linear regression line for soil sample 187.

FIG. (16) *a* and *b* depicts a direct assay curve and direct assay standard curve.

As used herein the term "antigen" is understood to be any substance capable of stimulating antibody production. In a like manner the term "diacyl hydrazine antigen" is understood to be any diacyl hydrazine compound capable of stimulating antibody production wherein the produced antibodies have binding affinity to diacyl hydrazines and derivatives thereof. Also, the term "immunogen" is understood to include any substance used to induce an immune response. The immunogen generally is comprised of a carrier molecule and a another constituent (hapten).

As used herein the term "measuring" is understood to encompass both qualitative analysis, i.e., identification of the presence of an analyte in a sample, as well as quantitative analysis, i.e., the determination of the amount of an analyte in a sample. It is also understood that such term may include the preparation of standards and standard curves, such preparation being well known in the art.

As used herein the term "diacyl hydrazine compounds" is understood to include within its scope diacyl hydrazines as well as metabolites, synthetic analogs, environmental degradates and photochemical degradates which are derived therefrom.

As used herein the term "$IC_{50}$" is defined as the concentration of the inhibitor required to reduce the absorbance to one-half the absorbance measured when no inhibitor was present. This determination is accomplished by plotting the percent (%) activity remaining versus the concentration of the inhibitor where the percent (%) activity remaining is given by:

$$\% \text{ activity} = (A_o - A_i / A_o) \times 100$$

where $A_o$ is the measured absorbance when no inhibitor is present and $A_i$ is the measured absorbance at the $i^{th}$ concentration of inhibitor. The percent inhibition is then given by the relationship 100–(% activity).

The percent cross reactivity was derived by the equation:

$$\% \text{ Cross-reactivity} = (IC_{50,5992} / IC_{50,analog}) \times 100$$

where $IC_{50,5992}$ is the $IC_{50}$ concentration for RH5992 as determined above and $IC_{50,analog}$ is the $IC_{50}$ concentration of the analog, i.e., RH2703, RH2651, and RH0345.

Sensitivity in ng is calculated from the concentration of the inhibitor determined from regression analysis of the standard deviations of the replicate analyses of the standard concentrations as described in the equation:

$$S = (Y_{int}/m) \times V$$

where S is the sensitivity in ng, $Y_{int}$ is the Y-intercept of the regression line from the standard deviations of the replicate analyses in absorbance units, m is the slope of the regression line in absorbance units per ng/ml and V is the volume of sample applied to the microtiter plate in ml.

Percent recovery is calculated from the relationship:

$$\%R = (C_0 C_a) \times 100$$

where $C_o$ is the observed (measured) concentration and $C_a$ is the actual (spike) concentration.

As recited above, an immunogen is provided which is useful in preparing antibodies to diacyl hydrazines. Generally, the immunogen includes a hapten and a carrier molecule.

The hapten is generally a diacyl hydrazine molecule or derivative thereof In one embodiment, the hapten is a benzoyl hydrazine. The benzoyl hydrazine compound is a compound according to formula (1) above.

Suitable examples of ($C_1$–$C_6$) alkyl include, but are not limited to, methyl, ethyl, n-propyl, isopropyl, n-butyl, isobutyl, tert-butyl, n-pentyl, isopentyl, neopentyl, n-hexyl, isohexyl, etc. Suitable examples of ($C_1$–$C_6$) substituted alkyl include, but are not limited to, methyl, ethyl, n-propyl, isopropyl, n-butyl, isobutyl, tert-butyl, n-pentyl, isopentyl, neopentyl, n-hexyl, etc., substituted with hydroxy, halide, ($C_1$–$C_4$) alkoxy, and nitro.

Suitable examples of ($C_2$–$C_6$) alkenyl include, but are not limited to, ethenyl, n-propenyl, isopropenyl, n-butenyl, isobutenyl, tert-butenyl, n-pentenyl, isopentenyl, neopentenyl, n-hexenyl, etc. Suitable examples of ($C_2$–$C_6$) substituted alkenyl include, but are not limited to, ethenyl, n-propenyl, isopropenyl, n-butenyl, isobutenyl, tert-butenyl, n-pentenyl, isopentenyl, neopentenyl, n-hexenyl, etc., substituted with hydroxy, halide, or nitro groups.

Suitable examples of ($C_1$–$C_6$) alkoxy include, but are not limited to, methoxy, ethoxy, n-propoxy, isopropoxy, n-butoxy, isobutoxy, tert-butoxy, n-pentoxy, isopentoxy, neopentoxy and n-hexoxy.

Suitable examples of ($C_1$–$C_6$) alkyloxy include, but are not limited to, carboxy (—COOH), acetyloxy (—$CH_2COOH$), propyloxy (—$CH_2CH_2COOH$), and n-butyloxy (—$CH_2CH_2CH_2COOH$).

Suitable examples of halides include, but are not limited to Cl-, Br-, F-, and I-.

In a preferred embodiment, R is —$CH_2COOH$, $R^1$ and $R^2$ are each methyl and $R^3$ and $R^4$ are each hydrogen. In a more preferred embodiment, R is —COOH, $R^1$ and $R^2$ are each methyl and $R^3$ and $R^4$ are each hydrogen.

The carrier material may be a protein, for example without limitation, bovine serum albumin, ovalbumin, or keyhole limpet hemocyanin; a polysaccharide, for example without limitation, dextran, sepharose, agarose or cellulose; or a synthetic polymer or copolymer, for example without limitation, polyacrolein, polyamide, polyacrylamide, polybutyrate, polyurea, polyureamide, or polystyrene.

In a preferred embodiment the carrier material is a carrier protein, more preferably bovine serum albumin (BSA) or keyhole limpet hemocyanin (KLH), most preferably keyhole limpet hemocyanin.

The immunogen of the present invention may be used to prepare antibodies to diacyl hydrazine compounds. The immunogen is introduced into a suitable animal and the antibodies collected, isolated and purified. The resultant antibodies are polyclonal antibodies having a high binding affinity and cross reactivity to diacyl hydrazine compounds and derivatives thereof, particularly benzoyl hydrazines and derivatives thereof Alternatively, the immunogen may be used to prepare monoclonal antibodies through use of hybridoma technology well known in the art.

In one embodiment, antibodies are raised to an immunogen of formula (1) conjugated to a carrier material. In a preferred embodiment, antibodies are raised to an immunogen of formula (1) wherein R is —$CH_3COOH$, $R^1$ and $R^2$ are methyl, $R^3$ and $R^4$ are hydrogen, conjugated to a carrier material. In a more preferred embodiment, antibodies are raised to an immunogen of formula (1) wherein R is —COOH, $R^1$ and $R^2$ are methyl, $R^3$ and $R^4$ are hydrogen, conjugated to a carrier material.

As recited above, the present invention provides a method of measuring diacyl hydrazines or derivatives thereof. Initially, the method includes in step (A) providing a sample comprising an unknown amount of diacyl hydrazine.

The sample is generally any material which may contain diacyl hydrazines. Suitable examples, include air, water, soil, and biological materials. In one embodiment, the sample may be an air sample or a sample derived from an air sample. In another embodiment, the sample may be a water sample or a sample derived from a water sample. In still another embodiment, the sample may be a soil sample or a sample derived from a soil sample.

In one embodiment, the sample may be a biological material or a sample containing a biological material or a sample derived from a biological material. Suitable examples of biological materials include without limitation, plant material; biological fluids such as blood, serum, plasma, lymphatic fluid, gastric lavage, bile, vitreous humor; biological tissues such as plant and animal tissues, and microbiological specimens such as bacteria and viruses.

In a preferred embodiment, the sample is a soil or plant material or a sample derived therefrom.

The diacyl hydrazine compound is as described above in Formula 1 as well as derivatives thereof Such derivatives may be, without limitation, metabolites, synthetic analogs, environmental degradates, photochemical degradates derived therefrom. Particularly useful diacyl hydrazines are benzoyl hydrazines according to Formula 1 which are depicted in Table 1 following.

TABLE 1

| Benzoyl hydrazine | R | $R^1$ | $R^2$ | $R^3$ | $R^4$ |
|---|---|---|---|---|---|
| RH5992 | —CH$_2$CH$_3$ | —CH$_3$ | —CH$_3$ | H | H |
| RH2485 | H | —CH$_3$ | —CH$_3$ | —CH$_3$ | —OCH$_3$ |
| RH2703 | —CH$_2$COOH | —CH$_3$ | —CH$_3$ | H | H |
| RH2651 | —COOH | —CH$_3$ | —CH$_3$ | H | H |
| RH0345 | —Cl | H | H | H | H |

The sample of step (A) is contacted in Step (B) with antibodies having binding affinity to diacyl hydrazines in the presence of an immobilized diacyl hydrazine antigen.

The antibodies are as described above, with antibodies raised from the immunogen comprising RH2651 conjugated to KLH being preferred.

The antigen of the immobilized diacyl hydrazine antigen may be any of the diacyl hydrazines described above conjugated to any of the carrier molecules described above. In a preferred embodiment the immobilized antigen is RH2651 or RH2703 conjugated to a carrier protein, more preferably RH2703 conjugated to BSA. The combination of the antigen and the carrier molecule is referred to as the coating antigen.

The coating antigen is generally immobilized on a solid support having a surface(s) which are amenable to attachment of such an antigen. Suitable examples include without limitation microtiter plates; membrane material such as nitrocellulose, cellulose, cellulose acetate, polycarbonate, etc.; test tubes; particles such as beads, column packing materials, etc.; and derivatized surfaces having binding domains capable of binding the antigen attached thereon. Generally, the coating antigen is applied to a solid support and adsorbed thereto.

In one embodiment, the coating antigen is adsorbed onto a microtiter plate.

In step (B) competition for binding sites on the antibodies having a high affinity for diacyl hydrazines occurs between the free antigen, i.e., the unknown quantity of benzoyl hydrazines in the sample, and the immobilized, i.e., bound, antigen. As a result bound and unbound antigen-antibody complexes are formed. In step (C) the bound complex is separated from the unbound complex. Separation may be by any means known in the art, such as without limitation gravity separation, magnetic separation, and washing to remove unbound complex.

Once separated from the unbound antigen-antibody complex the bound complex is labeled with a detectable label in step (I)). The label may be any material which can be fixed to the bound antigen-antibody complex and be detected. The label may be detected directly or indirectly through inter-action with a substrate. Suitable examples include without limitation enzymes, colored dyes, fluorescent materials, chemiluminescent materials, bioluminescent materials, and radioactive isotopes. In a preferred embodiment the detectable label is an enzyme. Generally, the enzyme is conjugated with a material which has a binding affinity to the bound antibody-antigen complex. The binding of the label to the complex may be by antibody-antigen, protein-ligand, or avidin(strepavidin)-biotin binding. In a preferred embodiment, the binding is antibody-antigen binding wherein the label is bound to an antibody having binding affinity for the bound antibody-antigen complex. Such binding results in a typical "sandwich" configuration well known in the art. The antibody bound to the label may be polyclonal or monoclonal. Furthermore, an antibody fragment of any of the above recited antibodies which contains the binding region of the antibody such as Fab fragments may be used. The particular antibody conjugated to the label will, of course, depend on the type of antibody conjugated to the antigen. That is, the antibody conjugated to the label will be chosen to have binding affinity to the immobilized antibody-antigen complex.

For instance, in a preferred embodiment the antibody conjugated to the antigen in the present invention is raised in rabbits. Consequently, the antibody conjugated to the label is an anti-rabbit antibody having binding affinity to the rabbit antibodies.

Once the immobilized antibody-antigen complex is labeled a measurable change is effected in the label in step (E). The measurable change may be effected by irradiation with uv-vis light, fluorescent, an electrical waveform, or introduction of a substrate which interacts with the label to produce a measurable change. It is understood that the measurable change may be inherent in the label, for instance, the label may be a radioactive isotope wherein radioactivity, e.g., gamma-rays, which may be effected simply by introducing means to measure the radioactivity.

In one embodiment, wherein the measurable change is effected by contacting the labeled complex with a substrate. Such substrates are well known in the art and of course are dependent on the type of label used. In a preferred embodiment, the label is an enzyme and the substrate is a compound capable of interacting with the enzyme to produce a measurable change. In a more preferred embodiment, the enzyme is a phosphatase and the substrate is a phosphate compound. The interaction of the enzyme and the substrate generally results in a compound having a measurable property. For instance, a compound which is fluorescent, has a strong absorbance, etc.

Finally, once the measurable change is effected in step (E), the diacyl hydrazines are measured in step M). Such measurement, is by methods known in the art, e.g., uv-vis spectrophotometry, fluorometry, gamma counting, etc.

The above recited assay is generally known as an indirect assay. Also, understood to be included within the scope of the present invention is a direct assay. Initially, the direct method includes in step (A) providing a sample comprising an unknown amount of diacyl hydrazines. The sample and diacyl hydrazines are as described above.

The sample of step (A) is contacted in Step (B) with immobilized antibodies having binding affinity to diacyl hydrazines to form immobilized antibody-diacyl hydrazine complexes. The antibodies are as described above with antibodies raised to RH2651 being preferred.

The antibodies are generally immobilized on a solid support having a surface(s) which are amenable to attachment of such an antibody. Suitable examples include without limitation microtiter plates; membrane material such as nitrocellulose, cellulose, cellulose acetate, polycarbonate, etc.; test tubes; particles such as beads, column packing materials, etc.; and derivatized surfaces having binding domains capable of binding the antibody attached thereon. In a preferred embodiment the antibody is a coating antibody which is fixed to a solid support as described above with reference to the coating antigen.

In step (B) binding sites on the immobilized polyclonal antibodies are filled by free antigen, i.e., the unknown quantity of benzoyl hydrazines in the sample, to form immobilized antibody-antigen complexes. In step (C) diacyl hydrazine antigen labeled with a detectable label is contacted with sites on the immobilized antibodies which were not bound to benzoyl hydrazine from the sample. Accordingly, the labeled antigen will fill the remaining binding sites on the antibodies. So that the immobilized antibodies will be conjugated to labeled and unlabeled antigen. The diacyl hydrazine antigen and label are as described above. However, in a preferred embodiment, the antigen is RH2651 and the label is an enzyme, preferably horseradish peroxidase (HRP).

Finally, in step (D) a measurable change is effected in the label and diacyl hydrazines are measured in step (E). Effecting of the measurable change and measuring of the diacyl hydrazines is as described above for the indirect assay.

The assays described herein for diacyl hydrazines such as RH5992 and its derivatives RH2703, RH2651, RH0345 and RH2485 are sufficiently sensitive for application to field residue studies as required by FIFRA registration. Moreover the assay has sufficient cross-reactivity with structurally dissimilar analogs such as RH0345 that it is believed that the assay will be applicable for the entire class of substituted N-t-butyl-N, N'-benzoyl hydrazine pesticides.

Aside from the sensitivity of the assay (parts per billion) and its general utility to the class of pesticides represented by RH5992, the greatest advantage may be the increased laboratory efficiency. For example, it has been shown that a single analyst can easily process twenty samples per day. This estimation includes sample preparation and results calculation. Assuming a ten hour day, only about 30 man-minutes per sample labor cost is incurred.

Additional uses for the antibodies of the present invention include binding the antibodies to a solid support to concentrate residues from samples matrices so they may be labeled with a fluorescent tag and be used in tissue studies to identify the location of pesticide residues in cellular compartments. This information provides important information as to the mode of action or mechanisms of toxicity and metabolism of the particular diacyl hydrazine compound. Also, the direct immunoassay method may be incorporated into a "dip-stick" test for field analysis and survey types of applications.

The following abreviations are used in the Examples following as well as in other portions of the specification.

| | |
|---|---|
| BCA | Bicinchoninic Acid |
| BSA | Bovine serum albumin |
| DCC | Dicyclohexylcarbodiimide |
| DEA | Diethanolamine |
| DMF | Dimethylformamide |
| HRP | Horseradish peroxidase |
| KLH | Keyhole Limpet Hemocyanin |
| NHS | N-Hydroxysuccinimide |
| PBS | Phosphate Buffered Saline |
| PBST | PBS and 0.01% TWEEN 20 Polysorbate |
| PNPP | para—nitrophenylphosphate |

EXAMPLE 1

Immunogen Synthesis

In a 5 ml pear shaped flask 21 µmole of hapten RH2651 was added to and dissolved in 200 µl DMF (Fisher Scientific). In separate 4 ml test tubes 16 mg DCC (EM Sciences) and 9.1 mg NHS (Sigma Chemical) were dissolved in 200 µl of DMF. The DCC and NHS were transferred to the flask containing the hapten and the reactants were allowed to stir at room temperature for approximately two hours. The reaction was transferred to a cold room to continue stirring overnight at 4° C.

Carrier Protein, KLH (Imject®, Pierce Chemical Co., 20 mg of protein in PBS (pH 7.2 when reconstituted) was reconstituted in 5.4 ml deionized water. The activated hapten was transferred to a microcentrifuge (Microcentrifuge Model 235B, Fisher Scientific) and centrifuged for 5 minutes to remove the substituted urea precipitate. The supernatant was transferred to the reconstituted carrier protein solution and stirring was continued at room temperature for four hours.

The protein reaction mixture was centrifuged @ 14000 rpm for 5 minutes to remove precipitated protein. The entire volume of the supernatant was applied to a Swift® polyacrylamide desalting column (Pierce Chemical Co.) and eluted with 0.01 M PBS (pH 7.3) in 3 ml fractions. Fractions were collected after the sample had been completely loaded onto the column. Ten three (3) ml fractions were taken and the absorbance at 280 nm was measured for each fraction. The fractions containing the immunogen were pooled and the protein concentration was measured by the BCA method (See BCA Protein Assay Reagent Instructions—Pierce Chemical Co.).

The hapten/protein binding ratio was determined as follows. A standard curve of the absorbance of KLH at 254 nm over the range of 0 µg/ml to 1200 µg/ml was established. The protein concentration of the immunogen fraction measured by the BCA method was converted to absorbance at 254 nm from the standard curve. A standard curve of the absorbance of the haptens RH2651 and RH2703 at 254 nm over the concentration range of 26 to 260 nmole/ml for RH2703 and 6.5 to 210 nmole for RH2651 was established.

The absorbance of the immunogen was measured at 254 nm ($A_{conj}$) and the calculated contribution to the absorbance at 254 nm from the KLH ($A_{KLH}$) was subtracted to give the absorbance arising from the hapten ($A_{Hap}$). This value, $A_{Hap}$, was converted to concentration (nmole/ml) from the standard curve for the hapten.

The molar binding ratio of hapten to protein was calculated from the calculated concentration of hapten (nmole/ml) divided by the measured concentration of immunogen. An average molecular weight for KLH of $6.7 \times 10^6$ dalton was used. The average number of hapten molecules per 10,000 amu of KLH was calculated by dividing the molar binding ratio by 670. The results are presented in Table 2.

EXAMPLE 2

Additional Immunogen Synthesis

An immunogen was prepared according to the procedure of Example 1, except that the hapten used was RH2703. Results are shown in Table 2.

EXAMPLE 3

Coating antigen Synthesis

Coating antigens (RH2703 and RH2651), were prepared according to the procedure for preparing the immunogen in Example 1 except that BSA (Imject®, Pierce Chemical Co.) replaced KLH as the carrier protein. The average molecular weight of BSA used in the calculation of molar binding ratio was 68,000 dalton. The average number of hapten molecules per 10,000 amu of BSA was calculated by dividing the molar binding ratio by 6.8. Results for the coating antigens prepared are shown in Table 2.

TABLE 2

| Sample | Protein µmole/ml | Hapten µmole/ml | Hapten/Protein | N[(1)] |
|---|---|---|---|---|
| RH2651-KLH | $2.8 \times 10^{-4}$ | 0.437 | 1560 | 2 |
| RH2703-KLH | $2.9 \times 10^{-4}$ | 0.943 | 3250 | 5 |
| RH2651-BSA | 0.03 | 1.5 | 50 | 7 |
| RH2703-BSA | 0.04 | 2.2 | 55 | 8 |

[(1)]N is the number of molecules of hapten per 10,000 amu of protein.

EXAMPLE 4

Production of Antibodies

A primary inoculum was prepared from 2.5 ml of the immunogen (product of Example 2 reconstituted to 1 mg/ml in 0.01M PBS), 25 mg *M. tuberculosis* suspension and 2.5 ml of Freund's adjuvant. The mixture was homogenized until thick and creamy.

New Zealand White rabbits (5) were used to produce antibodies. The rabbits were disease free females weighing between 4.75 to 5.5 pounds. The rabbits were first inoculated intramuscularly against *Bordetella pertussis* (*B. pertussis* inoculum prepared to contain $6 \times 10^{10}$ cells suspended in 0.6 ml saline) and bled to provide a background titer.

The dose of primary inoculum per rabbit was 1.0 ml by subcutaneous injection. The rabbits were inoculated and received booster immunizations every 21 days. Eight days after the fourth booster injection, the rabbits were bled to collect antibodies. After an additional time period, booster injections were reinitiated and a production bleed was done again after the fourth booster injection.

EXAMPLE 5

Assay of Rabbit Antisera

Coating antigen was reconstituted in coating buffer (PBS, pH 7.2) to an initial concentration of approximately 10 µg/ml. The wells of columns 1 and 2 of 96 well microtiter plates were reserved for control samples. Beginning with the wells in column 3, 200 µl of the coating antigen was added at the initial concentration. The wells in columns 4 through 12 contained 100 µl of coating buffer. A portion, 100 µl, of the coating antigen in the wells of column 3 were transferred and mixed with the coating buffer in the wells of column 4 and in this manner the coating antigen is serially diluted 1:2 with coating buffer in each subsequent column of wells. The dilution process was continued through column 11 which was a 1:256 dilution of the coating antigen. The final 100 µl µl was discarded. Wells in column 12 contained only coating buffer with no antigen as negative controls. Wells A1 and A2 were air blanks and did not receive reagents. Wells B1 and B2 were coated with coating antigen and were background wells. Wells C1 and C2 were coated with 100 µl of KLH in coating buffer (about 10 µg/ml) as positive controls. The remaining wells D1 through H2 were untreated. The plate thus prepared was sealed with sealing tape, covered, wrapped in plastic wrap and placed in the refrigerator for overnight incubation at 4° C.

After incubation overnight the plates were removed from the refrigerator and emptied. Unbound binding sites in the wells (except A1 and A2) were blocked with 300 µl of BSA blocking solution (1% BSA, pH 7.2 prepared from 1.0 g BSA dissolved in 100 ml PBS). This solution was incubated at room temperature for at least 10 minutes.

Test samples were diluted 1:1000 with blocking solution and 200 µl were applied to the wells in Row A beginning with well A3. The wells in rows B3 through H3 contained 100 µl blocking solution. The test samples (100 µl) in row A wells were transferred to row B wells and mixed thoroughly. In this manner samples were serially diluted 1:2 through the wells of row G3 (1:64000) and the final 100 µl was discarded. The wells of row H3 contained no antibody and were negative controls. The background wells B1 and B2 were incubated with 100 µl of pre-bleed sera that was diluted 1:500 with blocking solution. The positive control wells C1 and C2 were incubated with a 1:1000 dilution of the test sample. Plates were incubated with the test sample for approximately one hour.

After incubation the test samples were removed and the wells were washed with washing buffer. The wells were filled 4–5 times with buffer. During the third or fourth wash, the buffer was allowed to remain in the wells for a 3–5 minute soak before discarding. Goat, anti-rabbit IgG linked to alkaline phosphatase (Pierce Chemical Co.), 0.6 mg, was reconstituted with 1 ml 50% glycerol and diluted 1:5000 with blocking solution. This solution, 100 µl, was added to each well and the plate was incubated for at least one hour at room temperature. Excess anti-rabbit antibody was washed away and 100 µl of PNPP solution (5 mg PNPP dissolved in 8 ml deionized water and 2 ml DEA buffer) was added to each well. The plate was incubated 30 minutes at room temperature. Then 50 µl of 2N NaOH was added to stop the enzymatic reaction. The absorbance in each well was measured at 410 nm using a Dynatech MR5000 microtiter plate reader. The results are depicted in Table 3.

TABLE 3

| Immunogen | Rabbit # | Test Bleed #1 | Test Bleed #2 | Production Bleed #1 | Production Bleed #2 |
|---|---|---|---|---|---|
| RH2651-KLH | 1331 | 1/32000 | 1/64000 | 1/64000 | 1/128000 |
| " | 1332 | 1/32000 | 1/128000 | 1/64000 | 1/128000 |
| " | 1333 | 1/32000 | no bleed[2] | 1/64000 | 1/128000 |
| " | 1334 | 1/32000 | 1/64000 | 1/128000 | 1/128000 |
| " | 1335 | 1/32000 | 1/32000 | 1/128000 | 1/128000 |
| RH2703-KLH | 1336 | 1/16000 | 1/64000 | 1/64000 | 1/128000 |
| " | 1337 | 1/16000 | 1/64000 | 1/64000 | 1/128000 |
| " | 1338 | 1/16000 | 1/64000 | 1/64000 | 1/128000 |
| " | 1339 | 1/32000 | 1/64000 | 1/64000 | 1/128000 |
| " | 1340 | nd[1] | 1/64000 | 1/64000 | 1/128000 |

[1]Antibody titer was not determined.
[2]Ear scarring prevented the taking of a test bleed in this animal.

EXAMPLE 6

Isolation and Purification of Antibodies

Immune serum collected over the course of the injections in Example 3 were pooled and assayed for total protein by the BCA method and found to be 66 mg/ml. The volume of immune serum was measured and divided into two equal aliquots of 90 ml each. A single aliquot was diluted with two equivalent volumes of deionized water. The resulting solution volume was diluted in turn with an equal volume of 4M ammonium sulfate to give a final 2M ammonium sulfate solution. The suspension was allowed to stir overnight at room temperature. The protein precipitate was collected by centrifugation at 10,000 g-av. for thirty minutes. The protein pellet was dissolved in a minimum volume of 0.02M sodium phosphate buffer (pH 8.0) that had been prepared from dilution of 0.1M sodium phosphate buffer.

The reconstituted protein solution was dialyzed for four hours against 2L of 0.02M sodium phosphate buffer (pH 8) at room temperature, then overnight against 4L at 4° C., and finally for 4 hours against 4L at room temperature.

The ion exchange purification of IgG from the pooled antisera was conducted with two separate aliquots utilizing DEAE Cellulose (DE52, Whatman, Inc.), 150 ml wet volume, which was packed to a bed height of approximately 26 cm in a 2.6 cm (i.d.) column. The column was equilibrated to 0.02M sodium phosphate buffer (pH 8.0). The column had a protein capacity of approximately 1.5 g (10 mg per ml wet volume). The entire volume of the dialyzed protein solution was pumped onto the column and elution begun with 0.02M sodium phosphate buffer, pH 8.0. The flow rate was adjusted to approximately 5 ml/min and 5 ml fractions were taken. The first 150 ml effluent contained any unretained protein.

After the first 150 ml the molarity was continuously changed in a linear gradient to 0.3M. The gradient was formed in a two chamber gradient former containing 250 ml of 0.02M buffer in the first chamber and 250 ml of 0.3 ml buffer in the second chamber. The first chamber was continuously stirred during elution. The next 500 ml of effluent was collected in 5 ml fractions. The elution of protein was monitored by measuring the absorbance at 280 nm which was plotted against elution volume (fraction #) to give a chromatogram.

Aliquots of each fraction were assayed for IgG by the indirect method described herein. Fractions containing IgG were pooled and the volume was reduced using a stirred cell concentrator with an Amicon filter (molecular weight exclusion limit—10,000 dalton). The protein concentration of the pooled, concentrated IgG fraction was assayed by the standard BCA method. Sodium azide was added (0.02% w/v) to the protein solution which was sterile filtered and stored frozen at −20° C. The protein elution profile from the DEAE ion exchange column is depicted in FIG. 1. The open circles represent the total protein as measured from absorbance at 280 nm. The closed circles represent the antibody titer for each fraction as measured by the indirect assay at 410 nm. Fractions 51–80 were pooled for further purification by protein affinity chromatography.

The DEAE purified IgG (1 mg/ml) was affinity purified using Protein A AffinityPak® Columns and the ImmunPure® IgG Buffers (ImmunoPure® IgG Purification Kit, Pierce Chemical Co.). The protein A column and buffers were allowed to come to room temperature and the column was washed with 5 ml of Binding Buffer. The DEAE purified IgG was diluted 1:9 to give a protein concentration of 6 mg/ml and a 1 ml aliquot was applied to the column. The column was washed with another 15 ml of binding buffer.

Elution of the IgG was carried out with 5 ml of ImmunoPure® IgG Elution buffer and 1 ml fractions were taken. The absorbance of each fraction was measured at 280 nm and the fraction with significant absorbance (fraction 3) was desalted using a 5 ml Excellulose® column which had been previously conditioned with 10 ml of 0.02M PBS (20 mM sodium phosphate, 100 mM NaCl, pH 7.4). Ten one (1) ml aliquots of 0.02M PBS were used for elution and 1 ml fractions were collected. The absorbance of each fraction was assayed for total protein by the BCA method.

The Protein A affinity chromatography purified IgG was diluted 1:5 to give a protein concentration of 1 mg/ml. Given an estimated 9 mg/ml IgG concentration from an average total serum protein of 66 mg/ml the estimated recovery of IgG was 67 percent.

EXAMPLE 7

Optimization of Indirect Assay

RH2703-BSA was used as the coating antigen. The concentration required to give a readable response (0.3–0.5 absorbance units @ 410 nm) in the presence of the minimum quantity of antigen (RH2703) was optimized in the presence of a constant amount of protein A purified IgG (10 μl of a 20 μg/ml solution, 100 ng/well) by a checkerboard type assay (see Voller et al, Bull of World Health Organization, 53, 35 (1976)). The concentration of the Protein A purified IgG had been previously optimized in the presence of a constant amount of coating antigen (RH2703-BSA, 100 μl of a 10 μg/ml solution) to give a readable response to the minimum amount of RH5992.

Antibody concentration was optimized to be approximately 20 μg/ml (100 ng per micro well) and the coating antigen was optimized to be 25 ng/ml or 2.5 ng per micro well. When converted to a molar basis and assuming a hapten/protein binding ratio of 55, the hapten is in a three-fold molar excess of the IgG added.

The percent inhibition for RH2703, RH2651, RH5992, RH0345 and RH2485 were determined to the protein IgG in the presence of the optimized concentration of RH2703-BSA coating antigen. Each test substance was assayed at seven concentrations ranging from no test substance 0 ng/ml to 1000 ng/ml. The assay at each concentration was replicated seven times. Antigen negative and antibody negative wells provided negative controls while KLH/anti-KLH wells were used as positive controls.

Serial dilutions of the test substance stock solutions were made with coating buffer containing 0.1% TWEEN 20 polysorbate to give 1000 ng/ml, 100 ng/ml, 10 ng/ml, 1 ng/ml, 0.1 ng/ml, and 0.01 ng/ml assay concentrations. Coating buffer w/0.1% TWEEN 20 polysorbate was used as the 0 ng/ml assay concentration. The test substance assay concentrations (190 μl each) were incubated with 10 μl of the protein A IgG (20 μl/ml) for one hour at room temperature. After the incubation period, 100 μl of the test substance-IgG mixture was transferred to the appropriate microtiter well. The microtiter wells had been previously coated with the optimized concentration of RH2703-BSA and the excess protein binding sites were blocked with 0.3 ml of a 1% BSA solution in coating buffer. The plates were incubated for an additional hour at room temperature.

After the second incubation the plates were washed and goat, anti-rabbit immunoglobulin conjugated to alkaline phosphatase (0.6 mg reconstituted with 1 ml 50% glycerol and subsequently diluted with 1:5000 with blocking solution Pierce Chemical Co) was added. The plates were incubated, washed and PNPP substrate added as described in Example 5. No NaOH stop solution was added and the plates were allowed to develop for two hours before reading the absorbance at 410 nm. The inhibition curves are depicted in FIGS. 2 through 6. Specific data for purified antibody characterization is shown in Table 4.

$IC_{50}$ was determined as recited above. The plot of percent activity versus inhibitor concentration was analyzed by exponential curve fitting with Microsoft Excel© Analysis ToolPak (Microsoft Corporation, Copyright 1993). To calculate the $IC_{50}$, the exponential equation of the form $y=bm^n x$ was then solved for x when y was set equal to 50, i.e., 50% activity remaining or 50% inhibition. Graphics were performed using Microsoft Excel©, Ver 5.0 graphics (Microsoft Corporation, Copyright 1993).

Percent cross-reactivity was calculated from $IC_{50}$'s as recited above. A plot of the average absorbances of the seven replicate analysis obtained from the seven concentrations of the inhibitors was made using Microsoft Excel©, Ver 5.0 graphics (Microsoft Corporation, Copyright 1993). The linear dynamic range was visualized as the linear portion of the curve obtained from a plot of absorbances at 410 nm from the various inhibitor concentrations. Sensitivity was calculated as described above.

The limit of detection was defined as three times the measured background noise. To assess the background noise the standard deviations of the replicate analyses at each concentration of inhibitor were calculated and the least squares method of regression analysis was performed. The y-intercept of the regression line was taken as the background absorbance arising from noise. The background absorbance was multiplied by a factor of three and converted to the concentration of the inhibitor by division with the slope of the standard curve obtained over the linear range. The resulting concentration was defined as the detection limit of the inhibitor.

TABLE 4

| Test Substance | IC50, ng/ml | Sensitivity, ng | Detection limit ng/ml | Cross reactivity, % |
|---|---|---|---|---|
| RH5992 | 0.61 | 0.07 | 0.66 | 100 |
| RH2703 | 1.13 | 0.19 | 1.7 | 54 |
| RH2651 | 1.59 | 0.22 | 1.9 | 38 |
| RH0345 | 6.5 | 0.08 | 0.75 | 9 |
| RH2485 | 0.05 | 0.08 | 1.8 | NA |

EXAMPLES 8–19

Indirect Assay

Microtiter plates were coated with 100 μd/well of RH2703-BSA coating antigen (10 μg/ml) to give a 1 μg per well coating. The plates were incubated overnight at 4° C. The unbound protein binding sites were blocked prior to use with 300 μl/well of a 1% BSA solution in coating buffer.

Approximately 1 gram aliquots of samples of broccoli and soil were taken. Broccoli sample #03 (1.0191 g) and soil sample #49 (1.0180 g) were identified as the controls and were spiked with 50 ng or 500 ng of RH5992 to measure recovery. The sample identification and sample mass used are identified in Table 6 below.

The sample aliquots were placed in 25 ml conical centrifuge tubes and the recovery sample was spiked with 50 or 500 ng of RH5992 which was prepared from dilution of RH5992 stock standard (1 mg/ml in acetonitrile) with PBST.

Samples were extracted with 5 ml aliquots of PBST by sonication with a sonic cell disruptor (Sonicator®, Heat Systems, Inc. Model W-225R with a Model H-1 microtip probe) for three minutes at 80% power. The extraction mixture was centrifuged for five minutes at 4,000 g and the PBST layer was decanted. An aliquot of each sample was diluted with PBST to give a 1:100 dilution (broccoli samples) and a 1:500 dilution (soil samples) of the original sample extract.

Aliquots of the diluted samples (180 μl) were mixed with 10 μl of each of the RH5992 standards (2, 10, 20, 100, 200, and 2000 ng/ml) and IgG (10 μl) to give samples having a final RH5992 concentration of 0.1, 0.5, 1, 5, 10 and 100 ng/ml respectively. The samples were thoroughly mixed in borosilicate glass tubes arranged in the 12×8, 96 well format. Tubes corresponding to the antigen negative wells contained 10 μl of buffer. The tubes corresponding to the antibody negative wells had no IgG added and contained 100 ppb RH5992 in PBST. The tubes corresponding to the KLH positive controls were left empty.

After a one hour incubation period, 100 μl of the spiked sample was transferred to the microtiter plates and the incubation was continued for another hour.

After incubation the plates were washed as described previously and 100 μl of goat, anti-rabbit IgG conjugated to alkaline phosphatase was added and incubated at room temperature for one hour. After incubation the plates were again washed and 100 μl of PNPP substrate was added. Incubation with substrate continued for one to two hours and the absorbance was measured at 410 nm using a Dynatech MR5000 Microplate reader. The absorbance measured in the antigen negative wells was averaged and automatically subtracted from the test wells. In this manner absorbance arising from non-specific binding of the antibody was removed.

Residue levels in samples were quantitated by the method of standard additions. Inverse absorbance versus concentration of added inhibitor plots were obtained from the average inverse of the non-specific binding subtracted absorbances of the duplicate samples using Microsoft Excel©, Ver 5.0 graphics. The resulting data was fitted to an equation of the form y=mx+b using Microsoft Excel© Analysis ToolPak. In this relation y was the experimentally measured inverse absorbance, b was the constant, m was the calculated slope and x was the concentration of the added inhibitor. Standard errors for each data point relative to the calculated value from the estimated solution to the linear equation were calculated and outlying values were omitted from the final solution.

Sample concentrations were obtained by solving the linear equation for x when y was set equal to the inverse absorbance measured with no added inhibitor. The result was converted to total ng by multiplication with the corresponding dilution factor. The final result in ng/g was calculated by dividing the total ng by the mass of sample taken.

A standard curve was established for quantitation of sample residues by the external standard method. Exponential curve fitting and linear regression analyses were performed using Microsoft Excel© Analysis ToolPak. Percent recovery was calculated as described above.

Figure 7A:
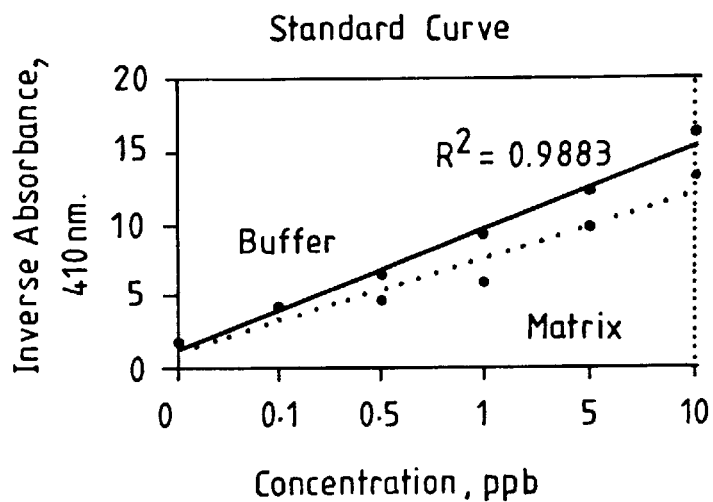
Figure 7B:
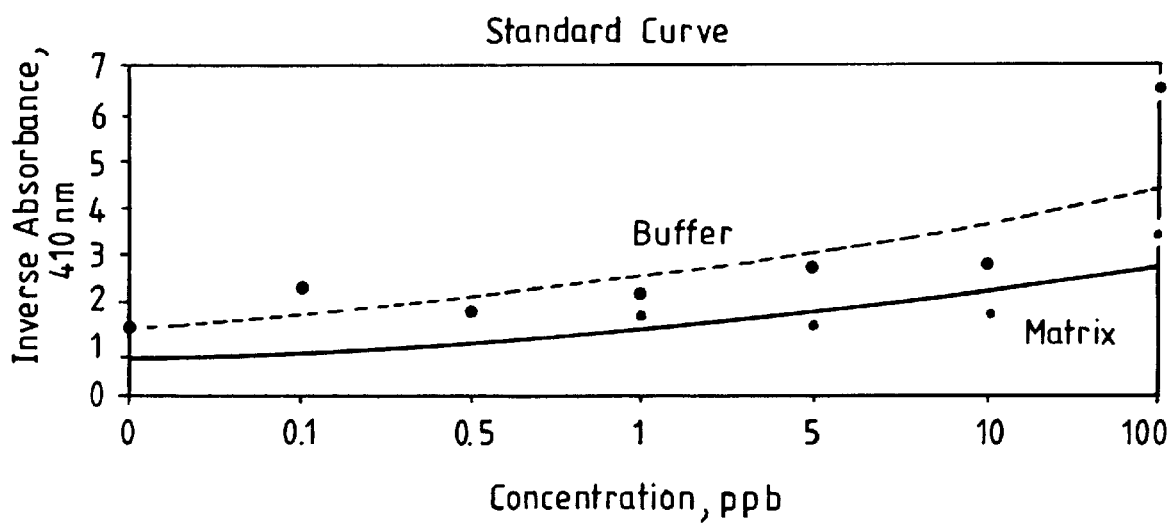
Figure 8:
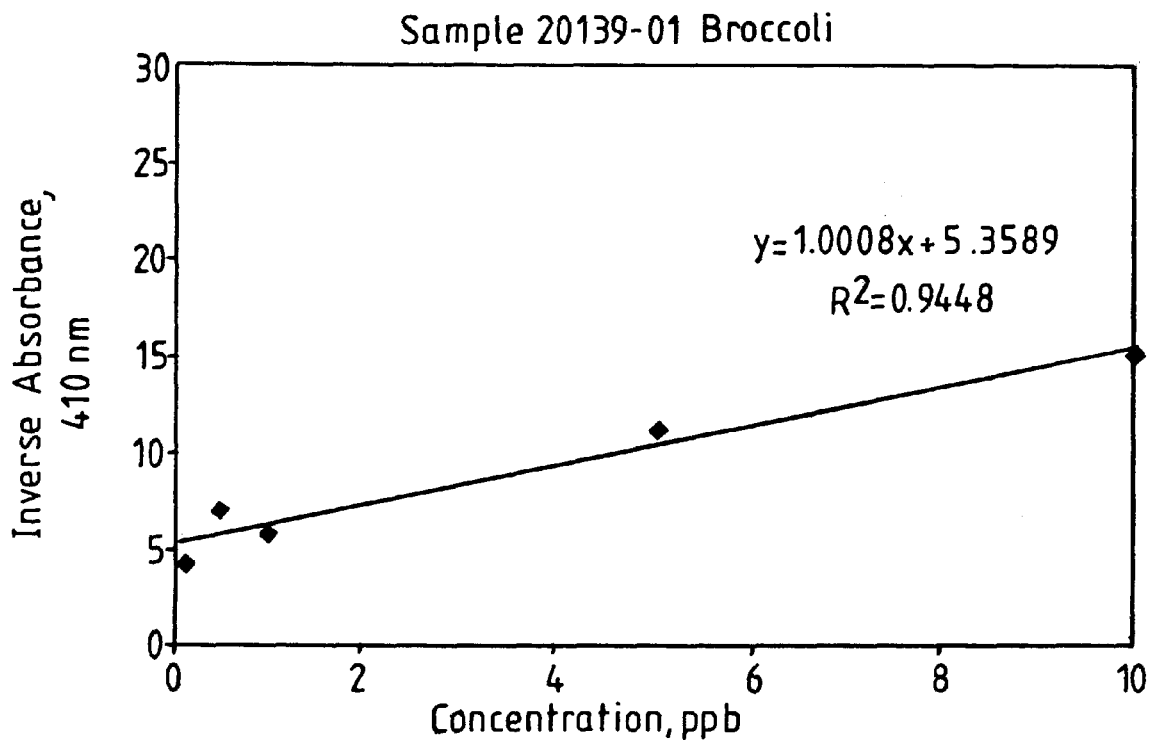
Figure 9:
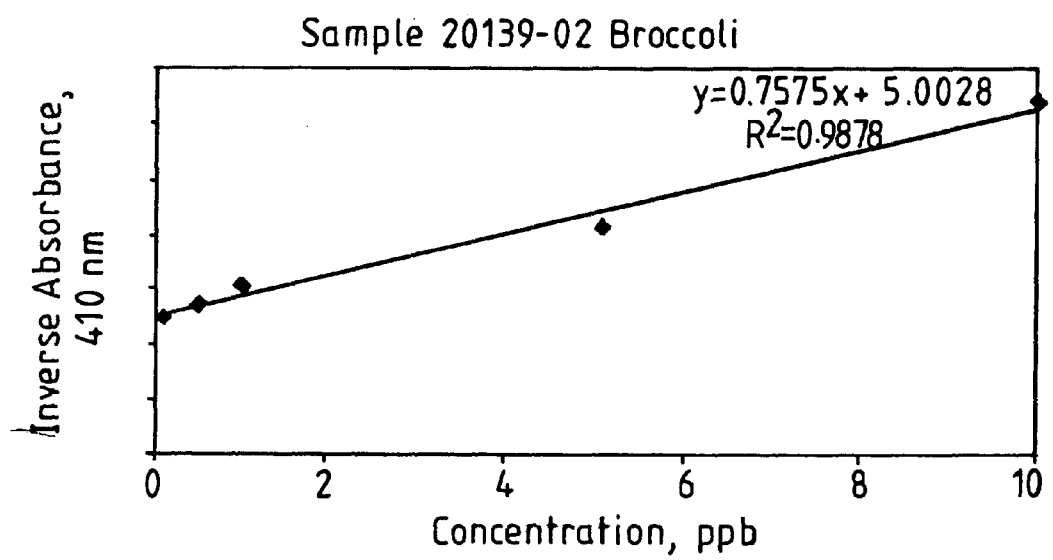
Figure 10:
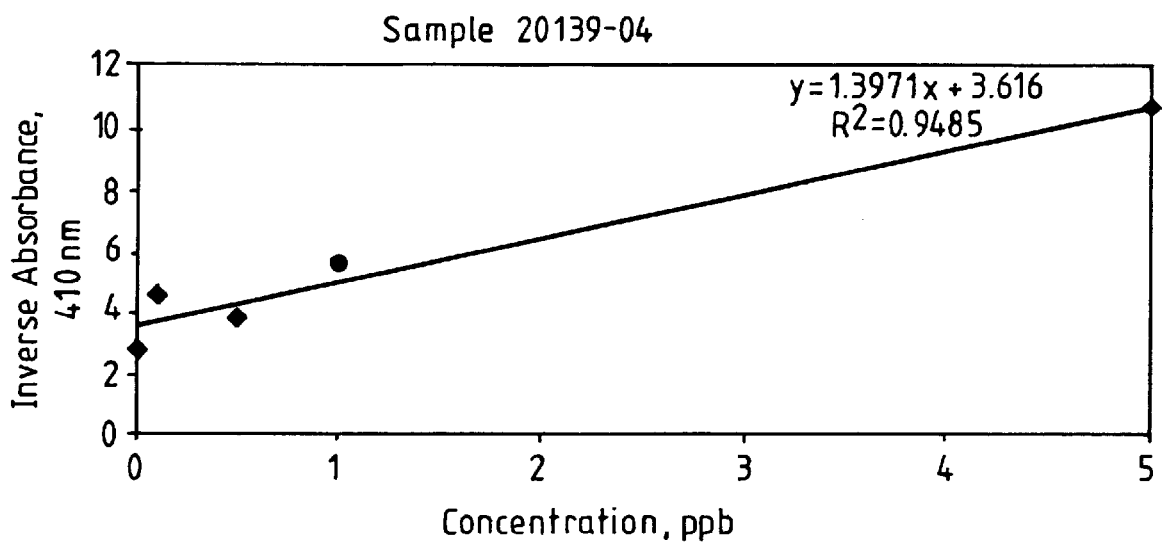
Figure 11:
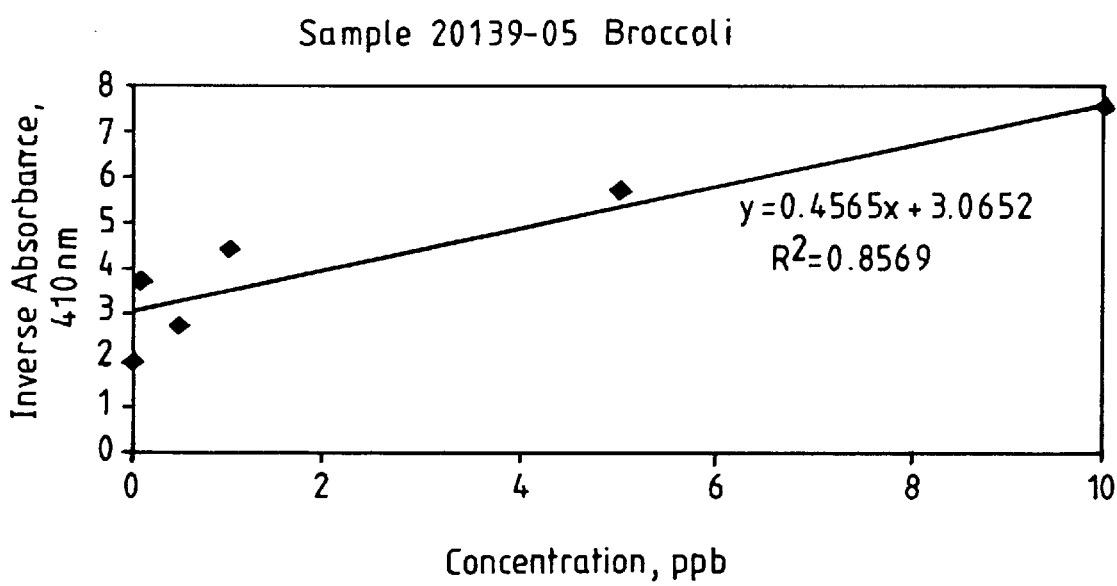
Figure 12:
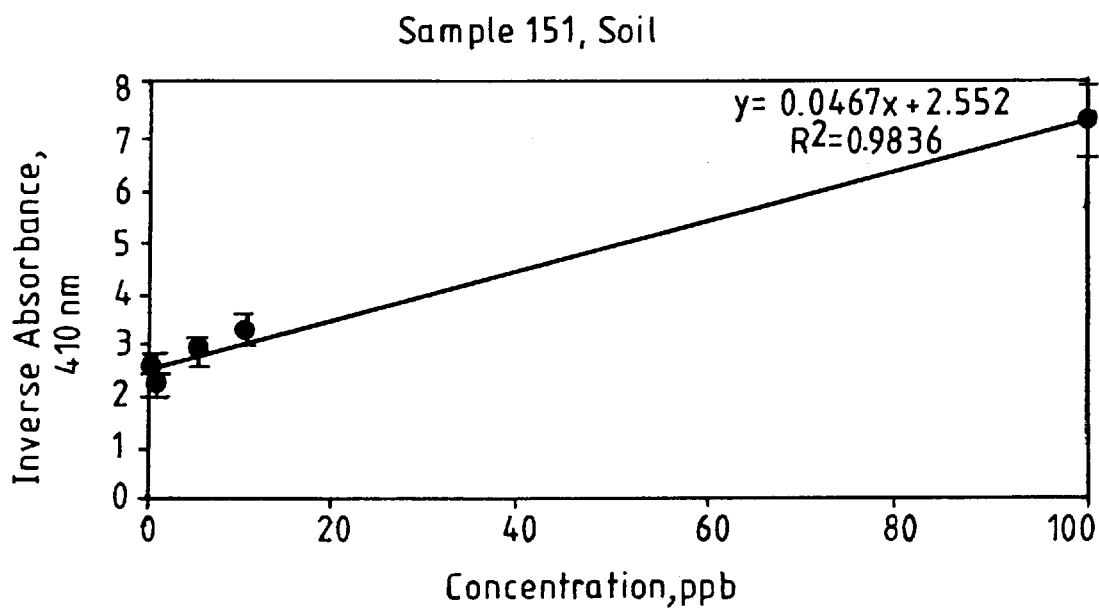
Figure 13:
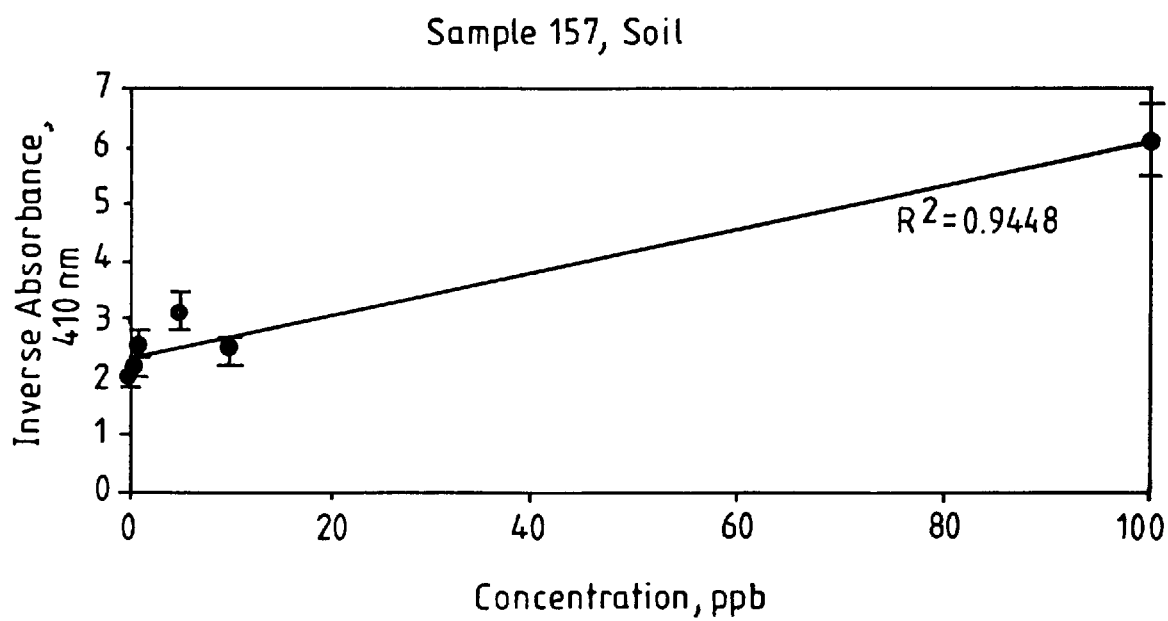
Figure 14:
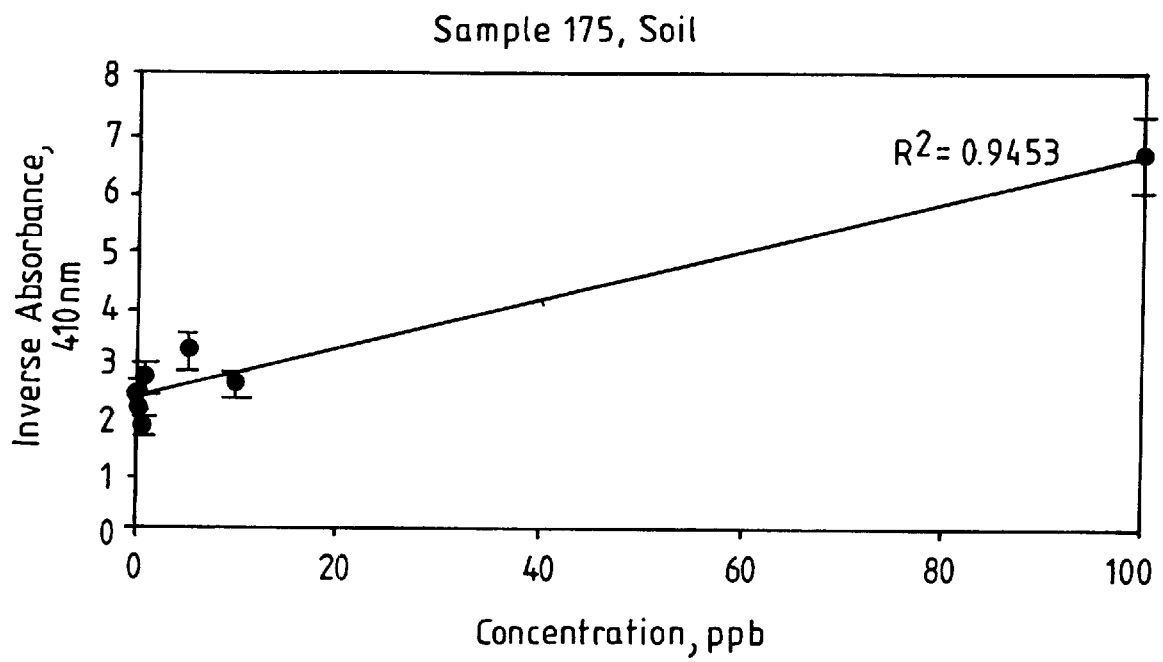
Figure 15:
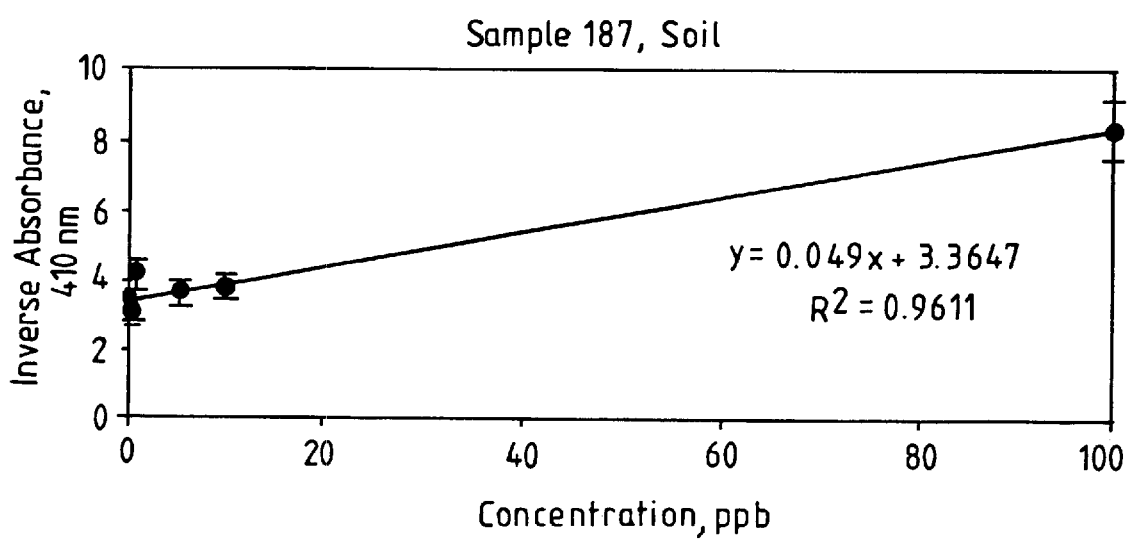

The recovery samples spiked at 50 ng/g and 500 ng/g were analyzed by both external standard and internal standard (method of addition) methods of analysis. The results with percent recoveries in parentheses are presented in Table 5. Plots of the standard curves obtained in PBST and matrix blank samples (broccoli sample #03 and soil sample #49) are presented in FIG. 7.

TABLE 5

| Sample | Internal Standard C ng/g | External Standard C ng/g |
|---|---|---|
| Broccoli $R_1$ | 52 (104%) | 53 (106%) |
| Broccoli $R_2$ | 471 (94%) | 426 (85%) |
| Soil $R_1$ | 55 (110%) | 55 (110%) |
| Soil $R_2$ | 511 (102%) | 514 (103%) |

The results from the internal standard analysis of the broccoli and soil samples are presented in Table 6. Two broccoli and soil extracts were reanalyzed a week later to evaluate the stability of the sample matrix. The results are presented in parentheses. Linear regression lines calculated for each sample are shown in FIGS. 8 through 15.

TABLE 6

| Sample ID Broccoli | C µg/g | Sample ID Soil | C µg/g |
|---|---|---|---|
| 20139-01 | 1.75 (1.41) | 92-0017-151 | 41.4 |
| 20139-02 | 2.41 | 92-0017-157 | 20.0 |
| 20139-04 | 5.92 | 92-0017-175 | 18.4 |
| 20139-05 | 13.2 (12.9) | 92-0017-187 | 28 |

EXAMPLE 20

Synthesis of Labeled Antigen

A 4.6 mg (10.5 µmole) quantity of RH2651 was placed in a 5 ml pear shaped flask and dissolved in 100 ml of DMF. In separate test tubes, 4.6 mg NHS and 8.8 µl DCC were dissolved in 100 µl each of DMF. The NHS and DCC were added to the RH2651 and stirred at room temperature for about one hour. Stirring was continued overnight at 4° C. The following day 10 mg HRP was dissolved in 2.7 ml 0.01M PBS, pH 7.2. The RH2651/NHS/DCC reaction mixture was centrifuged for three minutes in a Beckman Microfuge E (Beckman Instruments). The supernatant was added dropwise with stirring to the HRP. The mixture was stirred for 4 hours at room temperature and then centrifuged for 3 minutes in the microfuge. The supernatant containing the conjugated protein was desalted with a Swift® desalting column (Pierce Chemical Co.) equilibrated with PBS. The protein was eluted with PBS and 3 ml fractions were collected. Fractions containing the protein conjugate, as determined by absorbance at 280 nm, were pooled and the protein concentration was determined by the BCA Protein Assay (Pierce Chemical Co.).

Binding of RH2651 to HRP was confirmed as follows. Microplate wells were coated with 100 µl of 10 µg/ml 2651-HRP and stored at 4° C. overnight. After emptying the plate the wells were blocked with 1% BSA in PBS. After blocking, 1:2 serial dilutions of protein A purified 2651 IgG, prepared according to Example 6, (starting with 1:500) were added to the wells to probe for the RH2651. The plate was washed with 0.01% TWEEN 20 polysorbate PBS after a 1 hour room temperature incubation. Alkaline phosphatase labeled goat anti-rabbit IgG was added and incubated for an additional one hour at room temperature. The plate was washed and p-nitrophenylphosphate substrate added. After 15 minutes development time, the absorbance was measured at 410 nm with a Dynatech MR5000 Microplate Reader.

Evaluation of the conjugation of RH2651 to horseradish peroxidase demonstrated a titer of 1:32000 of the $^{2651}$IgG to 1 µg of 2651-HRP. This indicated a successful conjugation reaction.

EXAMPLE 21

Optimization of Coating Antibody

A microplate was coated with $^{2651}$IgG. Starting with column 1, 100 µl of 10 µg/ml $^{2651}$IgG were added to each well and 1:2 serial dilutions made across the plate. The plate was sealed and stored at 4° C. until ready to use. After emptying, the plate was washed with 0.01% Tween 20 in PBS and blocked with 1% BSA in PBS for about 1 hour at room temperature. After blocking, the plate was emptied and 150 µl PBS added to each well. Then 50 µl of 2651-HRP dilutions were added down the plate starting with 10 µg/ml and continuing with 1:2 dilutions down the plate. After a 1 hour room temperature incubation, the plate was washed as before and 150 µl 1-Step® Slow-TMB (peroxidase substrate from Pierce Chemical Co.) was added to each well. After one hour development, 150 µl of 1N $H_2SO_4$ was added to stop the reaction and the absorbance of each well measured at 450 nm with the Dynatech MR5000 Microplate Reader. Controls included wells with no coating antibody and wells in which no 2651-HRP were added. A $^{2651}$IgG coating antibody concentration of 0.625 µg/ml and a 2561-HRP concentration of 1.25 µg/ml were determined to be the optimum concentration for use with 1-Step® Slow-TMB substrate.

EXAMPLE 22

Direct Assay

The wells of a microplate were coated with 100 µl each of 0.625 µg/ml $^{2651}$IgG. One row was left uncoated as a control. The plate was kept at 4° C. overnight. The following day the plate was washed with 0.01% Tween 20 polysorbate in PBS and blocked with 1% BSA in PBS for at least 30 minutes. Standard solutions of RH5992, RH2651, RH2703, and RH2485 were made from 1 mg/ml stock solutions. Standard solutions of RH0345 were prepared from a 0.1 ng/ml, 0.5 ng/ml, 1 ng/ml, 5 ng/ml, 10 ng/ml, 50 ng/ml, and 100 ng/ml. After the blocking lo solution was emptied, 150 µl of the standards were added to the appropriate wells. For the zero control 150 µl of PBS was added. After a 45 minute incubation at room temperature, 50 µl of 1.25 µg/ml 2651-HRP were added to each well and the plate agitated to mix the contents. One column containing antibody and standards did not receive 2651-HRP but rather 50 µl PBS as a negative control. After incubation for 45 minutes at room temperature, the plate was washed as before and 150 µl 2651-HRP was added to each well and the plate agitated to mix the contents. One column containing antibody and standards did not receive 2651-HRP but rather 50 µl PBS as a negative control. After incubation for 45 minutes at room temperature, the plate was washed as before and 150 µl Step 1® Slow TMB added to each well. After 2 hours at room temperature, 150 µl 1N $H_2SO_4$ was added to each well and the absorbance read at 450 nm with the Dynatech MR5000 Microplate Reader.

Figure 16A:
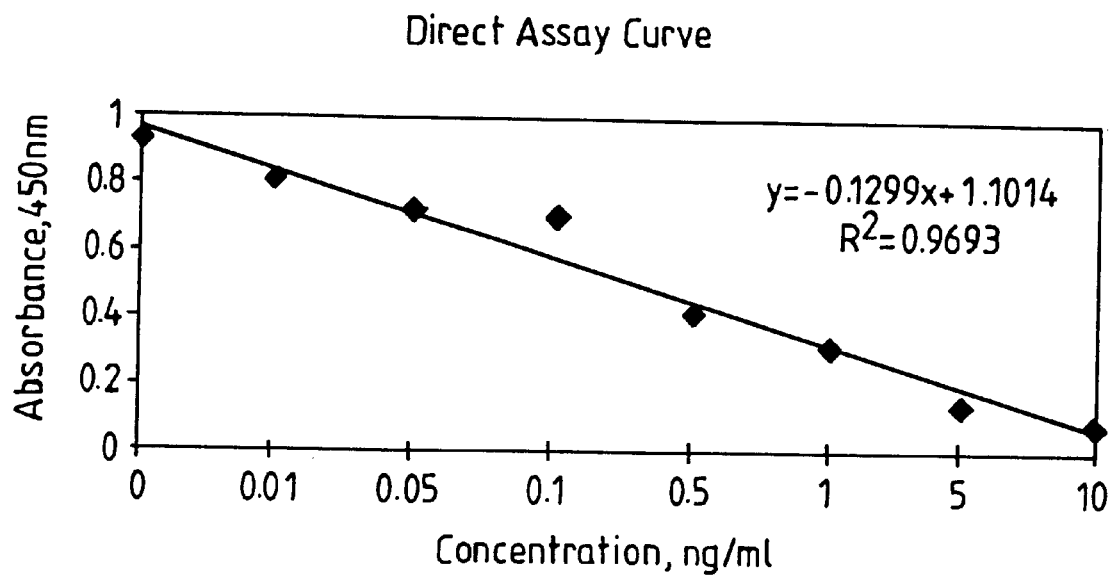
Figure 16B:
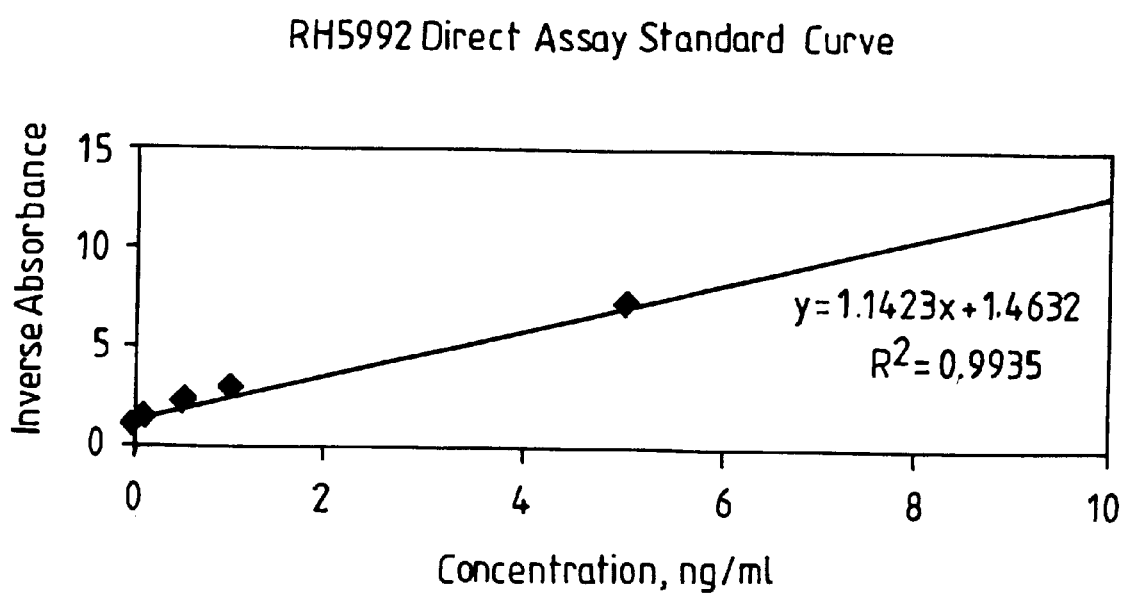

FIG. 16a illustrates a typical curve generated from the assay. The linear portion of the curve is visualized between 0.01 ng/ml and 10 ng/ml. A typical standard curve in the linear range of the assay is illustrated by FIG. 16b using inverse absorbances to generate a positive slope. The limit of detection was calculated as 0.096 ng/ml and the sensitivity calculated as 0.005 ng for RH5992. Data for RH5992 and analogs is given in Table 7.

TABLE 7

| Test Substance | IC50, ng/ml | Sensitivity, ng | Detection limit ng/ml | Cross reactivity ,% RH2651 | RH5992 |
|---|---|---|---|---|---|
| RH5992 | 3.64 | 0.005 | 0.106 | 32 | 100 |
| RH2703 | 2.10 | 0.002 | 0.031 | 56 | 173 |
| RH2651 | 1.17 | 0.001 | 0.013 | 100 | 311 |
| RH0345 | 16.94 | 0.255 | 5.10 | 6.9 | 21.5 |
| RH2485 | 4.64 | 0.024 | 0.482 | 25 | 78.4 |

We claim:

1. An immunogen, comprising:
a compound of the formula

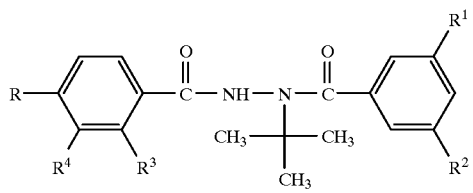

wherein R is —COOH or —CH$_2$COOH, R$^1$ and R$^2$ are methyl, and R$^3$ and R$^4$ are hydrogen; conjugated to a carrier material.

2. The immunogen of claim 1, wherein the carrier material is selected from the group consisting of protein, polysaccharide, synthetic polymer or copolymer.

3. The immunogen of claim 1, wherein R is —COOH.

4. The immunogen of claim 1, wherein R is —CH$_2$COOH.

5. Antibodies raised to the immunogen of claim 1.

6. Antibodies raised to the immunogen of claim 3.

7. Antibodies raised to the immunogen of claim 4.

8. The immunogen of claim 1, wherein the carrier material is a protein selected from the group consisting of bovine serum albumin, ovalbumin, and keyhole limpet hemocyanin.

9. The immunogen of claim 1, wherein the carrier material is a polysaccharide selected from the group consisting of dextran, sepharose, agarose, and cellulose.

10. The immunogen of claim 1, wherein the carrier material is a synthetic polymer or copolymer selected from the group consisting of polyacrolein, polyamide, polyacrylamide, polybutyrate, polyurea, polyureamide, and polystyrene.

11. The immunogen of claim 1, wherein R is —COOH and the carrier material is keyhole limpet hemocyanin.

12. Antibodies raised to the immunogen of claim 11.

13. A coating antigen, comprising:
a compound of the formula

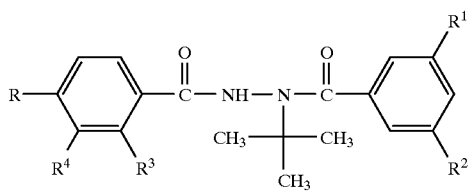

wherein R is —COOH or —CH$_2$COOH, R$^1$ and R$^2$ are methyl, and R$^3$ and R$^4$ are hydrogen; conjugated to a carrier material.

14. The coating antigen of claim 13, wherein the carrier material is selected from the group consisting of protein, polysaccharide, synthetic polymer or copolymer.

15. The coating antigen of claim 13, wherein R is —COOH.

16. The coating antigen of claim 13, wherein R is —CH$_2$COOH.

17. The coating antigen of claim 13, wherein the carrier material is a protein selected from the group consisting of bovine serum albumin, ovalbumin, and keyhole limpet hemocyanin.

18. The coating antigen of claim 13, wherein the carrier material is a polysaccharide selected from the group consisting of dextran, sepharose, agarose, and cellulose.

19. The coating antigen of claim 13, wherein the carrier material is a synthetic polymer or copolymer selected from the group consisting of polyacrolein, polyamide, polyacrylamide, polybutyrate, polyurea, polyureamide, and polystyrene.

20. The coating antigen of claim 13, wherein R is —CH$_2$COOH and the carrier material is bovine serum albumin.

* * * * *